(12) United States Patent
Monti, Jr.

(10) Patent No.: US 11,213,377 B2
(45) Date of Patent: Jan. 4, 2022

(54) INTEGRATED FLUID ADMINISTRATION SYSTEM

(71) Applicant: James H Monti, Jr., Plano, TX (US)

(72) Inventor: James H Monti, Jr., Plano, TX (US)

(73) Assignee: Quick Shot Corporation, Dallas, TX (US)

( * ) Notice: Subject to any disclaimer, the term of this patent is extended or adjusted under 35 U.S.C. 154(b) by 170 days.

(21) Appl. No.: 16/061,535

(22) PCT Filed: Nov. 17, 2015

(86) PCT No.: PCT/US2015/060981
§ 371 (c)(1),
(2) Date: Jun. 12, 2018

(87) PCT Pub. No.: WO2017/086924
PCT Pub. Date: May 26, 2017

(65) Prior Publication Data
US 2020/0261199 A1    Aug. 20, 2020

(51) Int. Cl.
*A61D 7/00* (2006.01)
*A61D 1/06* (2006.01)
*A61M 5/168* (2006.01)

(52) U.S. Cl.
CPC ............... *A61D 7/00* (2013.01); *A61D 1/06* (2013.01); *A61M 5/16804* (2013.01);
(Continued)

(58) Field of Classification Search
CPC . A61D 7/00; A61M 5/16804; A61M 2205/52; A61M 2205/8206; A61M 2250/00; A61M 5/427; A61M 2005/206
See application file for complete search history.

(56) References Cited

U.S. PATENT DOCUMENTS 5,322,511 A * 6/1994 Armbruster ............. A61M 5/20
604/155
7,414,534 B1 * 8/2008 Kroll .................... A61B 5/0031
340/573.1
(Continued)

FOREIGN PATENT DOCUMENTS

| EP | WO2012019641 | 2/2012 |
| WO | WO2014100658 | 6/2014 |
| WO | WO2014107766 | 7/2014 |

OTHER PUBLICATIONS

Australian Examination Report (App. No. 2015414726), IP Australia, dated Jan. 27, 2021.
(Continued)

*Primary Examiner* — Bradley J Osinski
(74) *Attorney, Agent, or Firm* — Regitz Mavck PLLC; Mike Regitz; Dustin Mavck

(57) ABSTRACT

Method and device to inject fluid into animals through a sterile needle, requiring control of fluid volume, flow rate of injection, accuracy of injection site, depth of penetration, disposal administration of consumable materials and quality control of the fluid and fluid administration using a portable applicator controlled by an external software controlled pump and controller system used in administering fluid medications, organic castration compounds and other fluids to be administered to live animals.

16 Claims, 13 Drawing Sheets

(52) U.S. Cl.
CPC ..... *A61M 2205/14* (2013.01); *A61M 2205/18* (2013.01); *A61M 2205/3576* (2013.01); *A61M 2205/52* (2013.01); *A61M 2205/581* (2013.01); *A61M 2205/582* (2013.01); *A61M 2205/587* (2013.01); *A61M 2205/6054* (2013.01); *A61M 2205/6072* (2013.01); *A61M 2205/8206* (2013.01); *A61M 2250/00* (2013.01)

(56) References Cited

U.S. PATENT DOCUMENTS

| | | | |
|---|---|---|---|
| 7,927,307 B2* | 4/2011 | D'Antonio | A61M 5/30 |
| | | | 604/152 |
| 8,864,713 B2 | 10/2014 | D'Antonio et al. | |
| 9,775,697 B2 | 10/2017 | Buckley et al. | |
| 2002/0107501 A1 | 8/2002 | Smith et al. | |
| 2006/0042633 A1* | 3/2006 | Bishop | A61B 5/0836 |
| | | | 128/207.18 |
| 2009/0299328 A1 | 12/2009 | Mudd et al. | |
| 2011/0054304 A1* | 3/2011 | Markowitz | A61B 34/20 |
| | | | 600/424 |
| 2011/0224613 A1 | 9/2011 | D'Antonio et al. | |
| 2014/0005596 A1 | 1/2014 | Schuster | |
| 2014/0142507 A1 | 5/2014 | Armes et al. | |
| 2015/0290392 A1 | 10/2015 | Henderson et al. | |
| 2016/0038266 A1 | 2/2016 | Edwards | |
| 2016/0184520 A1* | 6/2016 | Veyrent | A61M 5/2033 |
| | | | 604/503 |
| 2016/0324613 A1* | 11/2016 | Halamish | A61D 1/025 |
| 2016/0338816 A1 | 11/2016 | Buckley et al. | |

OTHER PUBLICATIONS

PCT Written Opinion of the International Searching Authority (PCT/US2015/060981), International Searching Authority, dated Jan. 13, 2016.

PCT International Preliminary Report on Patentability (PCT/US2015/060981), International Searching Authority, dated May 22, 2018.

PCT International Search Report (PCT/US2015/060981), International Searching Authority, dated Jan. 13, 2016.

Foreign Office Action (App. No. 3,007,456), Canadian Patent Office, dated Apr. 15, 2019.

Foreign Office Action (App. No. 3,007,456), Canadian Patent Office, dated Feb. 26, 2020.

Corrected Foreign Office Action (App. No. 3,007,456), Canadian Patent Office, dated Feb. 26, 2020.

European Search Opinion (App. No. EP 15 908 921.8), European Patent Office, dated Jun. 11, 2019.

Supplementary European Search Report (App. No. EP 15 908 921.8), European Patent Office, dated Jun. 11, 2019.

* cited by examiner

INTEGRATED FLUID ADMINISTRATION SYSTEM

FIELD OF INVENTION

This invention relates to a portable device which mechanically inserts a needle into animal flesh, muscle or organs at a controlled rate of insertion, to a specific depth of insertion, to inject a measured amount of fluid over a predetermined duration at a controlled flow rate; and, then retracts the needle. The device can record RFID tag information identifying the animal, timestamp injections applied to the animal and record injection record information as a downloadable file from the device.

BACKGROUND OF INVENTION

Ranchers and veterinarians often times need to administer injections to livestock. Various procedures for administering injections exist and include procedures such as subcutaneously (SQ; under the skin), intramuscularly (IM; directly into the blood supply of the muscle), or intravenously (IV; directly into the vein, usually the jugular vein) injections. Such injection procedures are useful when administering vaccinations, treating livestock with medications or delivering other drugs or chemicals to the animal.

When administering injections to livestock, multiple techniques have developed over time. The effectiveness of any particular technique is determined by factors including: 1) location where technique is suitable; 2) competence required of the administrator; 3) and, the resulting impact to health and comfort of the animal during and after the injection.

Injections can be administered by either using a syringe or with a dosing gun. When using a syringe, the administrator controls the injection by selecting the injection site, penetrating the syringe into the tissue and dispensing the volume of fluid specified for the injection. Competence is essential to properly administer injections using a syringe.

Consisting of three major components, the syringe has a barrel, plunger and needle. The capacity of the barrel is determinant to establishing the dosing which may be accomplished using the syringe.

An alternative to the syringe is to use a dispensing gun. Unlike using a syringe, a dosing gun dispenses a per-determined fluid volume to one or many animals. The dosing gun can be equipped with a vial of fluid, a needle and an actuator to manipulate the action of the dosing gun to perform the injection when activated.

The present embodiment described herein represents a dispensing gun which automates procedural elements associated with performing injections to livestock. The dispensing gun herein also combines multiple tasks which are necessary to implement when administering injections to livestock.

The present embodiment consists of applicator, database, logic processes, control mechanisms and a computerized controller module, which when assembled is battery powered for portability. The dispensing gun present in the present embodiment has been developed to overcome shortfalls and limitations commonly found in existing syringe or dosing gun techniques.

For example, frequently it is necessary to administer multiple doses to a single animal due to the limitation of the volume of fluid contained within the injection instrument. The present embodiment introduces a continuous flow pump to eliminate such limitations found in other instruments.

The present embodiment also meets a common need to administer multiple injections in different locations to the same animal. Since the insertion depth of the needle is determined by the location of the injection site on the animal, the dispensing gun present in the present embodiment has variable needle insertion depth control to ensure proper needle insertion angle, depth and duration for the injection required.

The present embodiment consists of computer control, database information stored in electronic memory and RFID (Radio Frequency Identification) functionality which provides for automated dosing level administration, safety and quality control, and dosing tracking and reporting. An integrated Barcode reader can be used to read a material description from the material vial, into the processor unit. The present embodiment has integrated controls which operate to improve and maintain high quality and safety standards for the care and protection of the livestock being injected.

The present embodiment also improves the efficiency of administering injections to large groups of animals. By using automated control functions implemented in the dispensing gun presented herein, ranchers and veterinarians may find it more economical to administer injections to livestock using this dispensing techniques based on the reduced stress to the animal accomplished by reducing the cycle-time to administer the injection to the animal; and, by increasing the number of animals injected per unit of time reduces the time the herd is gathered and thereby reduces the risk of injury to animals in confined spaces.

Automating dosing and needle manipulation functions reduces errors in application of the injection which result in increased yield effectiveness of the injections performed. Reduced error rates and increased yield lowers costs.

The present embodiment also provides a form factor suitable to use in the field. The dispensing solution presented herein can be worn by the user in a comfortable way or laid out on a table or bench for use. The dispensing solution is provided with a Tote Bag containing all the system components consisting of: belt system, hand-piece, sample disposable, system cable, pump/processor module, batteries, battery charger, and quick reference card). The User is intended to wear the pump/processor module in a belt pouch system for easy access and use. The belt pouch system includes a webbed belt for easy adjustment, quick operation and good support, a sturdy pouch to hold the pump/processor module, and an additional vial of the dispensable material, as well as a holster to hold the system hand-piece. The pouch and holster will be ambidextrous, so the user can fit their personnel needs. Also two belt pouch systems could be combined to permit a user to wear two systems and administer two fluids to an animal.

Although there are several apparatuses which may have various functions related to the integrated fluid administration system, none of these either separately or in combination with each other, teach or anticipate the current invention. Therefore, there remains an unmet need in the field of livestock injection dispensing devices. The current invention will fulfill this unmet need.

SUMMARY OF INVENTION

The following presents a simplified summary in order to provide a basic understanding of some aspects of the disclosed invention. This summary is not an extensive overview, and it is not intended to identify key/critical elements or to delineate the scope thereof. Its sole purpose is to present some concepts in a simplified form as a prelude to the more detailed description that is presented later.

The present embodiment consists of an integrated pumping and processor unit which contains the battery, pump, display, control panel, bubble sensor, vial attachment, and processor PCB, and may include by illustration and not limitation, a cable with connectors to connect signals to a hand-piece. The processor PCB assembly supports an integrated RFID reader module and corresponding antenna to read an animal RFID tags, whose number would be included in a stored record of the injection. The processor PCB assembly can also support an integrated Barcode reader module to read fluid information labels on the vials of liquid material being dispensed.

There will be a disposable that will be in a sterilized pouch and provides the supply needle, the delivery tubing, the injection needle or needles. The disposable would be used daily, and disposed of at the end of each working day. Through the use of the bubble sensor, the disposable will be sensed (no tube, dry tube, wet tube, bubble present, tube primed). Because of desired pumping accuracy, the disposable is a onetime use, during a single 12 to 16-hour day, on a single calendar day.

The present embodiment is a portable device powered by a rechargeable battery pack. A ~12 v custom lithium battery pack, or similar technology, with a two slot battery charging station will be included in the system. The battery pack will be easily changeable and is located in the pump/processor portion of the assembly.

The system initialization of the present embodiment is switch controlled. An LED, which can be a two or three color LED (like red, yellow, and green), will indicate the system status, at a glance. The same status is displayed on both the pump/processor unit, and the hand-piece. If the hand-piece is not attached to the pump/processor unit, the base unit will request that all components be assembled for system checks to be completed. When the unit is powered up, the display can provide information status for several items at the same time.

The initial power up of the day would check battery condition first, the check to see if a disposable is in place, if so, is the disposable wet or dry, if wet the screen will require a new disposable be inserted for the day's use. (Note: that the system should know if the disposable was in place at the end of the day "power down", so it could have that reference at startup the next day of use.) Once the disposable is current, the display could display several items, such as Battery level, injection volume, and "priming" vs "on/ready". The pump/processor will provide directions to complete each required step in the use of the IFAS, including the barcode reading labels of the material being dispensed.

The control panel will display startup information (battery level, self-test, disposable status, etc.), if a disposable is in place (test with the bubble sensor), and ready to prime, or replace, if left from the previous day. If no disposable is present, the system will prompt the loading of the disposable, priming of the disposable, then drive the "on/run" functions. Once the "on/run" status is reached, the LED and laser pointed could be started automatically or turned on manually.

A monitor feature could be included to turn "off" the power completely after a designated time (say a week), where the monitor voltage would be stopped. A unit in long term storage would require a fresh battery be placed in the unit, and the voltage spike would assist in initializing the unit for the first time of use.

The present embodiment implements software to control the injection cycle routine which advances the needle during the administration of the injection to the animal. The speed of insertion of the needle is adjustable, so we can mimic a veterinarian inserting the needle. The material will be injected (power the stepper motor, a timed amount for specific fluid volume, at a specific speed of injection) will be permitted. The needle injection depth can also be adjusted during injection, where desired by the animal type, and other injection criteria. The end of cycle will end with the retraction of the needle using a homing routine implemented in software. If the momentary button were released early, the injection would stop, and the needle would retract to the home position, and provide the "Error" indicators (LED color, Displayed Error note and vibrating motor).

The hand-piece provides the user interface to dispense the material. The needle and its delivery components will be retained in the Hand-piece. The hand-piece will contain a stepper screw drive to move the needle, a cart (carriage) running on a set of ribs to deliver the needle to the delivery site, an LED for use as a flashlight, an LED (multicolor) to indicate status, vibrating motor, a momentary switch and pressure ring as a safe function, and a laser pointer.

The hand-piece component of the present embodiment will contain a "contact/pressure" ring surrounding the exit point for the needle that must be pressed against the injection site, and held against the injection site, to activate the injection cycle. If the device were held in such a way that the function (injection) button were depressed without actuating the "contact/pressure" ring, the pumping cycle would not begin, and an error tone/vibration and red blinking LED would be initiated. After the "contact/pressure" ring is pressed against the injection site, the function (injection) button is pressed and held to start and complete the injection cycle.

The present embodiment is software controlled. The IFAS will have a software load for a single animal (pig, beef, goat, lamb, etc.). This software load can be loaded from the production software interface from the manufacturer laptop/calibration station and which can be exchanged when utilizing the system with different species animals.

The present embodiment may also be configured with a software load that suitable for use among multiple species, which would require a display screen during startup to select the animal being injected, hence the disposable and dosages required for that animal only. The IFAS can be used to inject other materials such as anti-bionics, or any other desired fluid.

The present embodiment is compatible with the use of animal RFID tags implemented for quality control and tracking purposes. The present embodiment software records an animal RFID tag and log a time stamp referenced to that RFID tag number and provide a paperless record of the fluid administration complete for a given set of animals in a given work day. This data is uploaded off the pump/processor module, on a daily basis, with either USB cable or with a secure wireless access. The present embodiment also supports a live interface from the IFAS to a wireless connection. This connection would be used to compare the scanned RFID tag with a central database of animals, for the ranch, corporation, etc., that would prevent the wrong material being injected in a particular animal.

For selection of the dose size, the dosage would be selected with the selection buttons and the Display will provide the method to set and indicate injection volume that the user would have access to. The permission for volume adjustment will be determined thru permission provided in the software load. Also the speed of the LP/stepper motor should be adjustable as well, to mimic the clinical examples.

The present embodiment shown herein can be worn by the user in a comfortable way or laid out for use. A tote bag containing all the system components belt system, hand-piece, sample disposable, system cable, pump/processor module, batteries, battery charger, and quick reference card). The user is intended to wear the pump/processor module in a belt pouch system for easy access and use. The belt pouch system includes a webbed belt for easy adjustment, quick operation and good support, a sturdy pouch to hold the pump/processor module, and an additional vial of the dispensable material, as well as a holster to hold the system hand-piece. The pouch and holster will be ambidextrous, so the user can fit their personnel needs. Also two belt pouch systems could be combined to permit a user to wear two systems and administer two fluids to an animal.

There are several methods currently used today to administer injections to livestock utilizing dosing guns. The present invention does not alter or disable this functionality.

Still other objects of the present invention will become readily apparent to those skilled in this art from the following description wherein there is shown and described the embodiments of this invention, simply by way of illustration of the best modes suited to carry out the invention. As it will be realized, the invention is capable of other different embodiments and its several details are capable of modifications in various obvious aspects all without departing from the scope of the invention. Accordingly, the drawing and descriptions will be regarded as illustrative in nature and not as restrictive.

BRIEF DESCRIPTION OF THE DRAWINGS

Various exemplary embodiments of this invention will be described in detail, wherein like reference numerals refer to identical or similar components, with reference to the following figures, wherein.

DETAILED DESCRIPTION

The claimed subject matter is now described with reference to the drawings. In the following description, for purposes of explanation, numerous specific details are set forth in order to provide a thorough understanding of the claimed subject matter. It may be evident; however, that the claimed subject matter may be practiced with or without any combination of these specific details, without departing from the spirit and scope of this invention and the claims.

Figure 1:
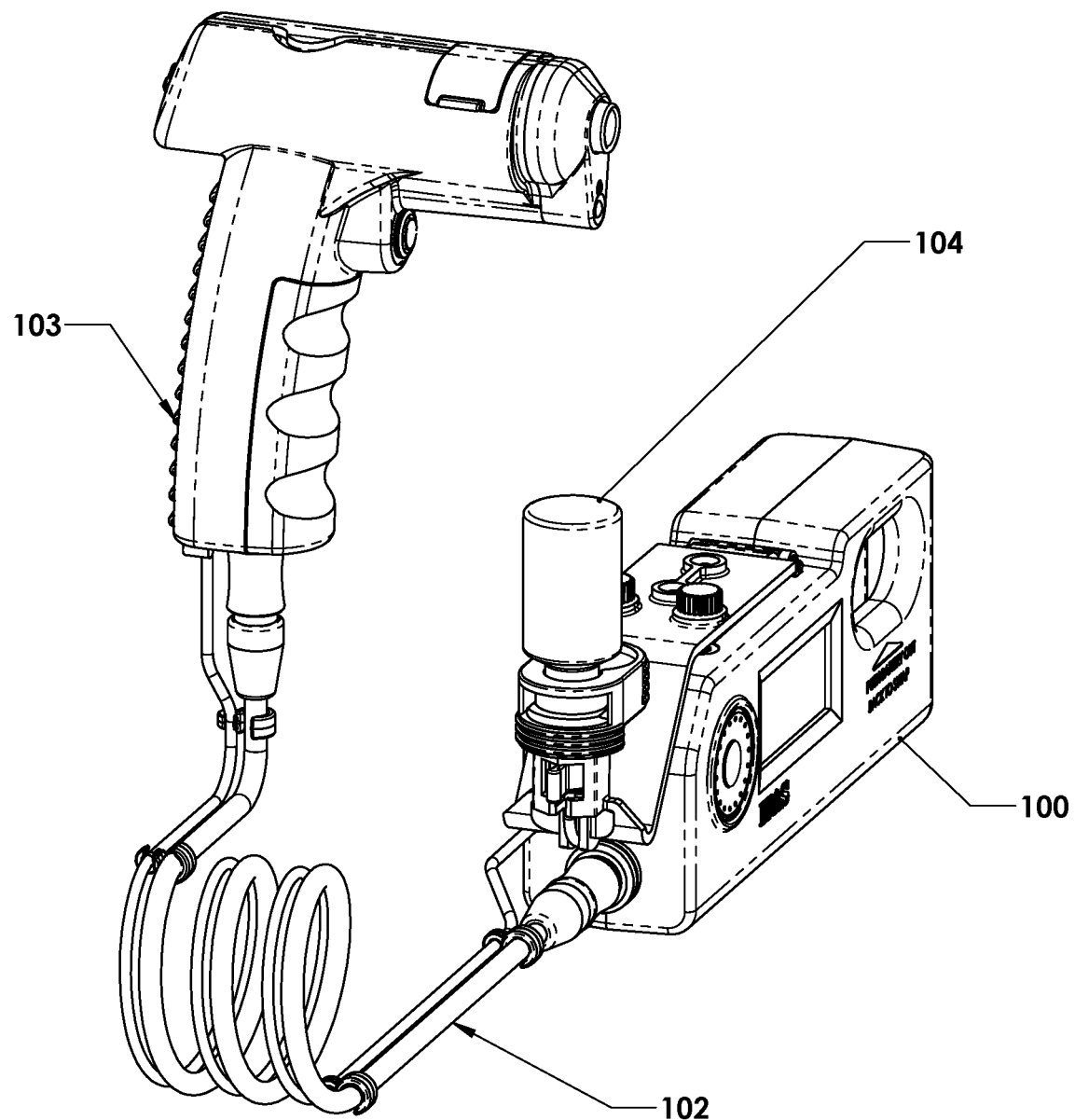
FIG. 1 is a perspective view of the preferred embodiment illustrated as portable system with a handheld applicator device, feed tube and pump control module.

In FIG. 1, the present embodiment is illustrated as pump/processor module 100, vial 104, hand-piece connector cable 102 and hand-piece 103. These components as shown collectively illustrate the integrated fluid administration system as a portable system.

The IFAS can be worn by the user in a comfortable way or laid out for use. The IFAS consists of the system components (hand-piece 103, hand-piece connector cable 102, pump/processor module 100, battery 312) and a battery charger, quick reference card, sample disposable, belt system and tote bag. The user is intended to wear the pump/processor module 100 in a belt pouch system for easy access and use. The belt pouch system includes a webbed belt for easy adjustment, quick operation and good support, a sturdy pouch to hold the pump/processor module 100, and an additional vial of the dispensable material, as well as a holster to hold the hand-piece. The pouch and holster will be ambidextrous, so the user can fit their personnel needs. Also two belt pouch systems could be combined to permit a user to wear two systems and administer two fluids to a single animal.

For the software load. The initial versions of the IFAS may have a software load for a single animal (pig, beef, goat, lamb, etc.). This software load can be loaded from the production software interface from the manufacturer laptop/calibration station. The first two loads are expected to be pig and beef. With additional animals to follow. The dosage and insertion needle, for the goat and lamb should be similar to the pig load, with additional animals as good candidates for the castration method and other drug administration. The type of animal is not limited by this description.

The IFAS can be used to inject other materials such as anti-bionics, or any other desired fluid. A software load, that might contain multiple uses, could provide all the envisioned functions. Also, as the market evolves, the use of animal RFID tags may become a desired control tool. The IFAS could record an animal RFID tag and log a time stamp referenced to that RFID tag number to provide a paperless record of the fluid administration complete for a given set of animals in a given work day. This data could be uploaded off the pump/processor module 100, on a daily basis, with either USB cable or with a secure wireless access by way of illustration.

There should also be a future capability to have a live interface from the IFAS to a wireless connection. This connection would be used to compare the scanned RFID tag with a central database of animals, for the ranch, corporation, etc., that would prevent the wrong material being injected in a given animal. In the same respect, an integral barcode reader may be used with the label data provided on the vials of material being dispensed to be entered into the processor unit from the barcode provided by the material vendor. An example could be a ranch raising both beef and pork, where two IFAS units are configured for a same day use. One IFAS system is loaded for beef castration, while the other IFAS system is loaded for piglet castration.

For example, a ranch hand has moved from the pig barns to the cattle barn in an outlying field and selects an IFAS unit, and then attempts to perform an injection on a calf with RFID tags. The IFAS unit will read the RFID Tag, comparing the tag number to the total database and sound an alarm reflecting a mismatch between the target animal being a calf and the current IFAS unit which is loaded with pig castration material. The resulting action will be an automatic disabling of the IFAS unit to prevent dispensing the incorrect material to the calf. Additionally, the LED indicators on the hand-piece will indicate an error to the user. To assist the user, the display on the IFAS would display the material content which is loaded in the unit when the unit is retrieved after laying idle.

Figure 2A:
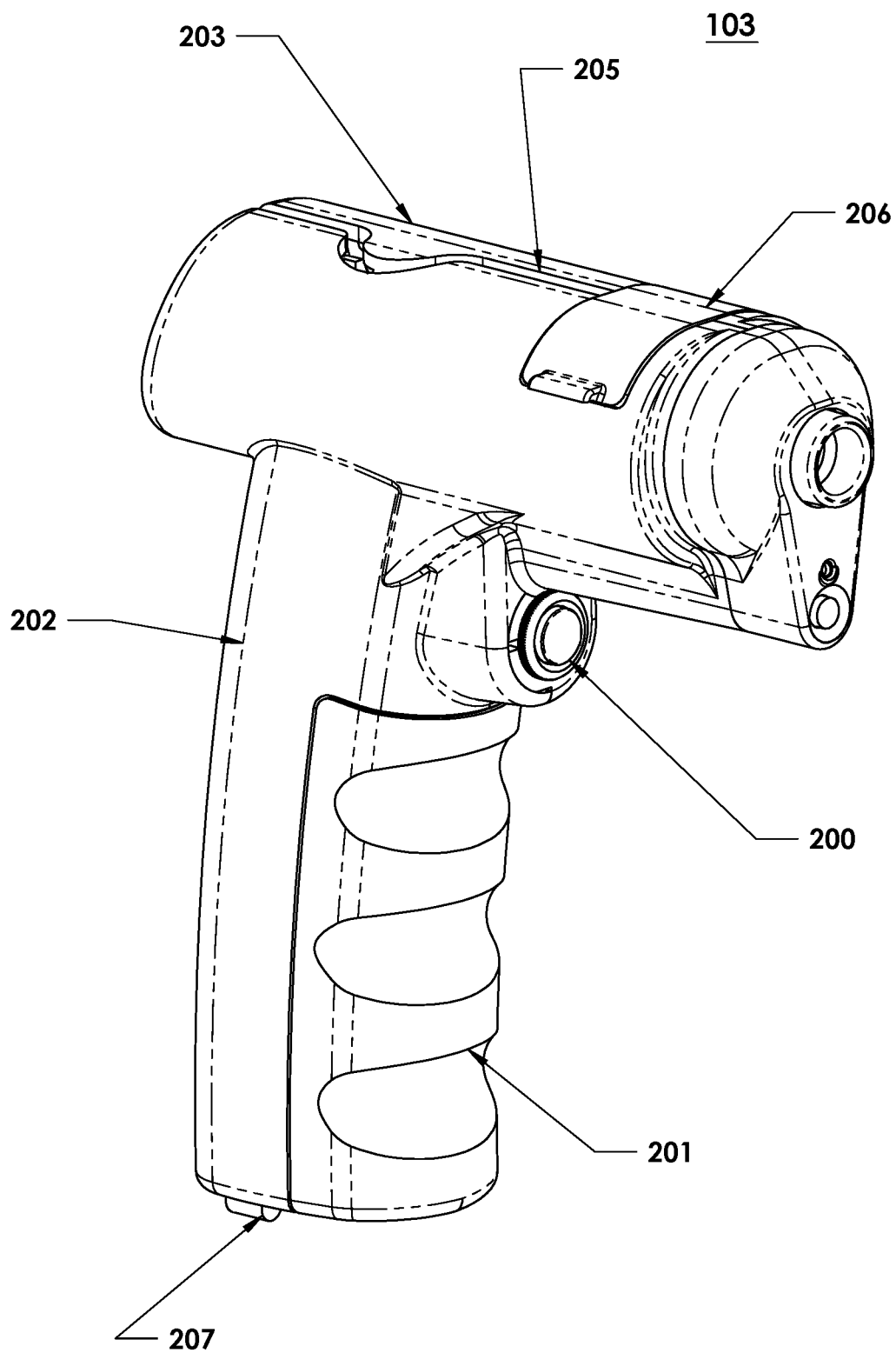
FIG. 2a is a front perspective view of preferred embodiment illustrating the handheld applicator device.
Figure 2B:
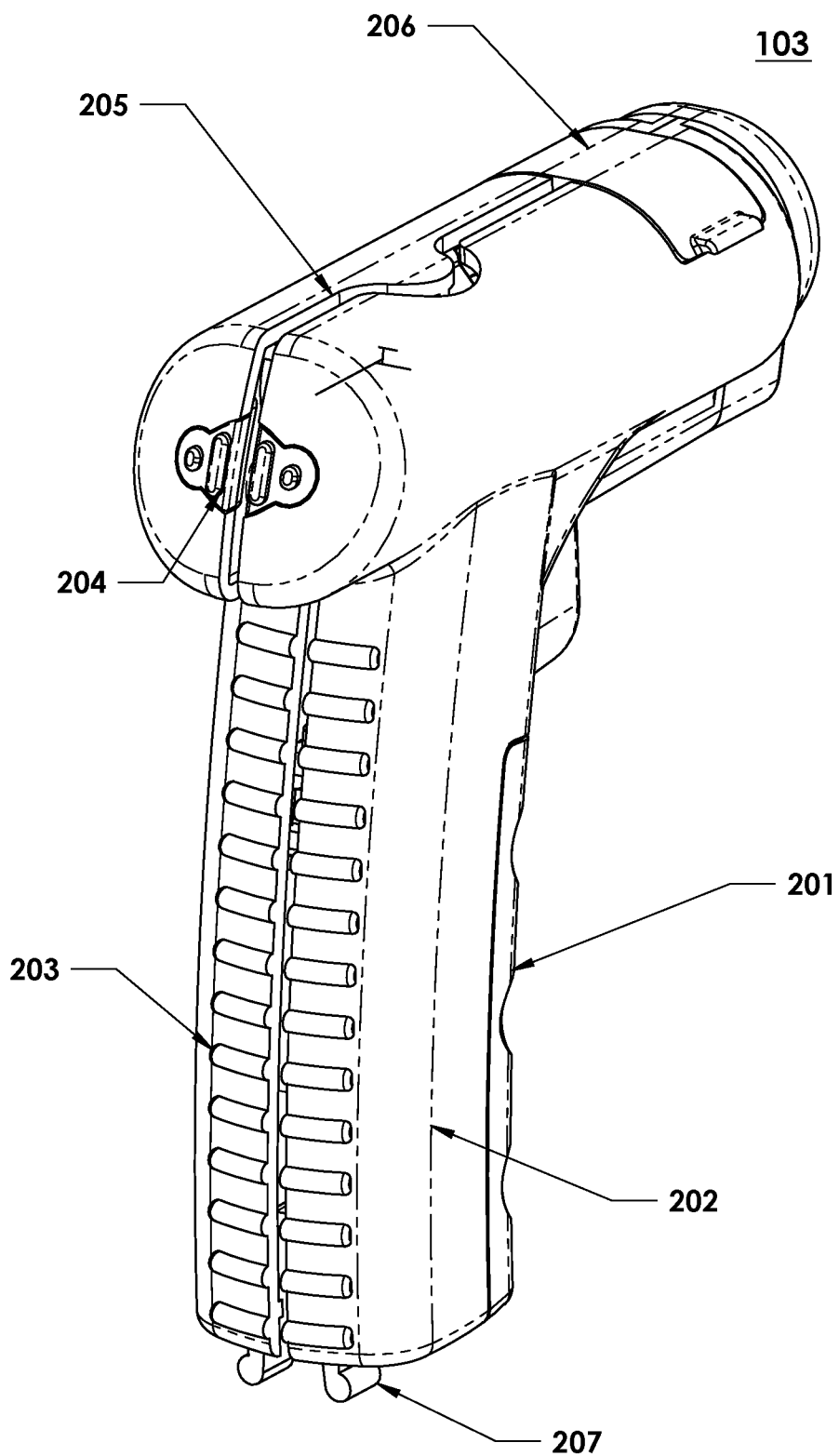
FIG. 2b is a rear perspective view of preferred embodiment illustrating the handheld applicator device.

In FIG. 2a, the hand-piece is illustrated from an external point of view locating the activation switch 200, soft over-molded finger grip 201, right side outer shell 202, left side outer shell 203, disposable slot 205, needle carrier access door 206 and disposable hand-piece retention clip 207. In FIG. 2b, the hand-piece is illustrated from a reverse exterior angle locating the LED indicator lenses 204 in addition to the elements described above.

Figure 3A:
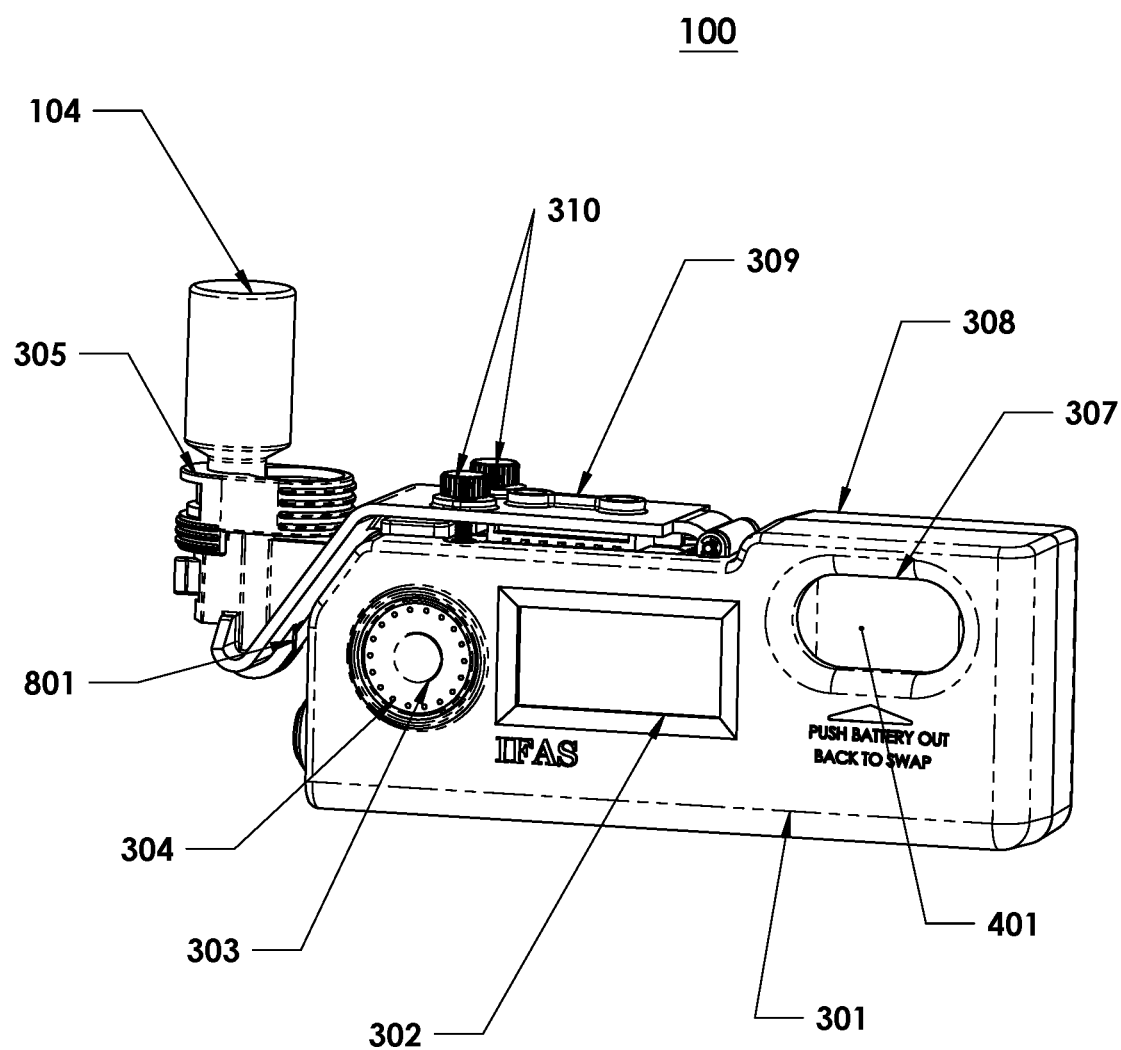
FIG. 3a is a front side perspective view of the preferred embodiment illustrating the pump control module.
Figure 3B:
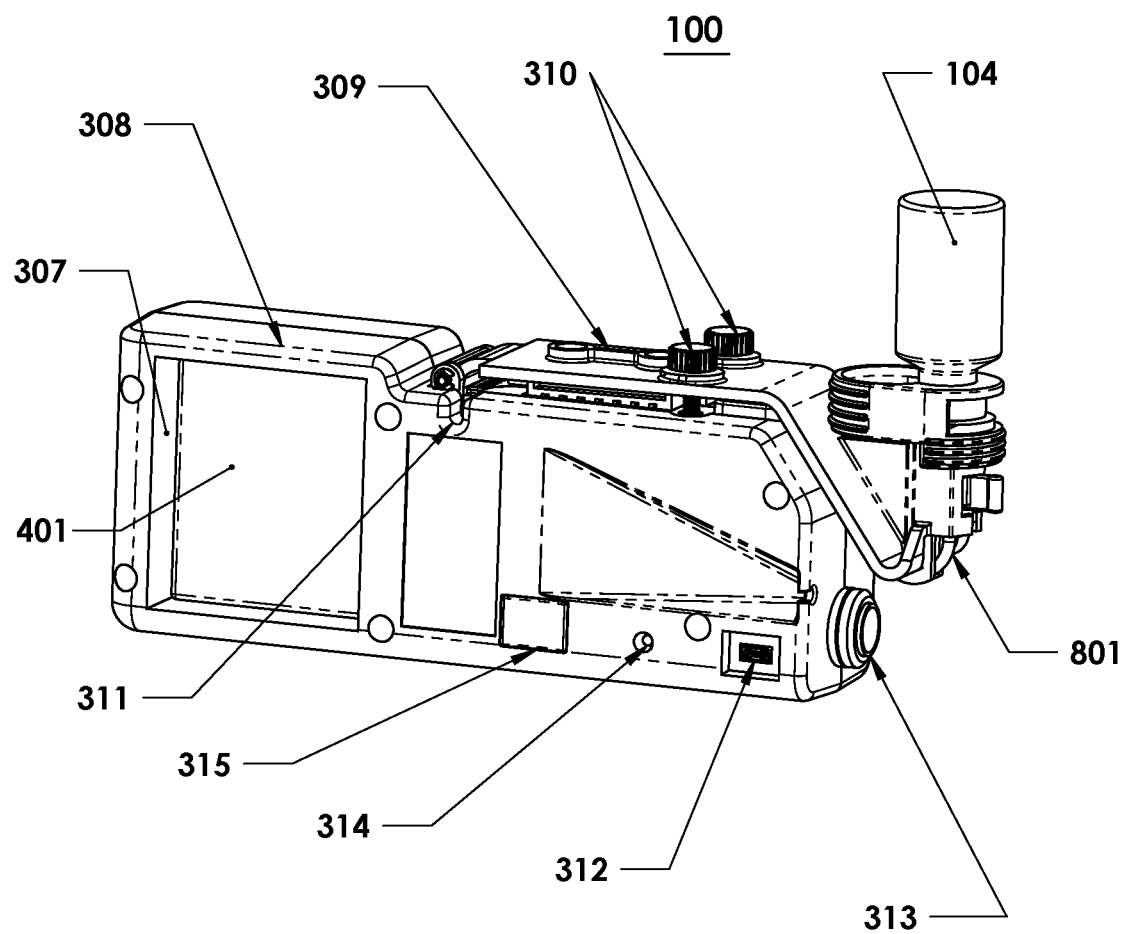
FIG. 3b is a rear side perspective view of the preferred embodiment illustrating the pump control module.

In FIG. 3a, the preferred embodiment pump/processor module 100 is shown with a frontal view with elements including outer front shell 301, display 302, pick button 303, selector wheel 304, vial lock 305, vial 104, battery slot 307, outer back shell 308, platen frame 309 and platen hold down screw 310. In FIG. 3b, the system control 100, FIG. 1, is shown with a rear view with elements including battery slot 307, outer back shell 308, platen frame 309, platen hold down screw 310, disposable exit slot 311, USB cable connector 312, hand-piece connector cable 313, on/off power switch 314 and barcode reader lens 315.

Figure 8A:
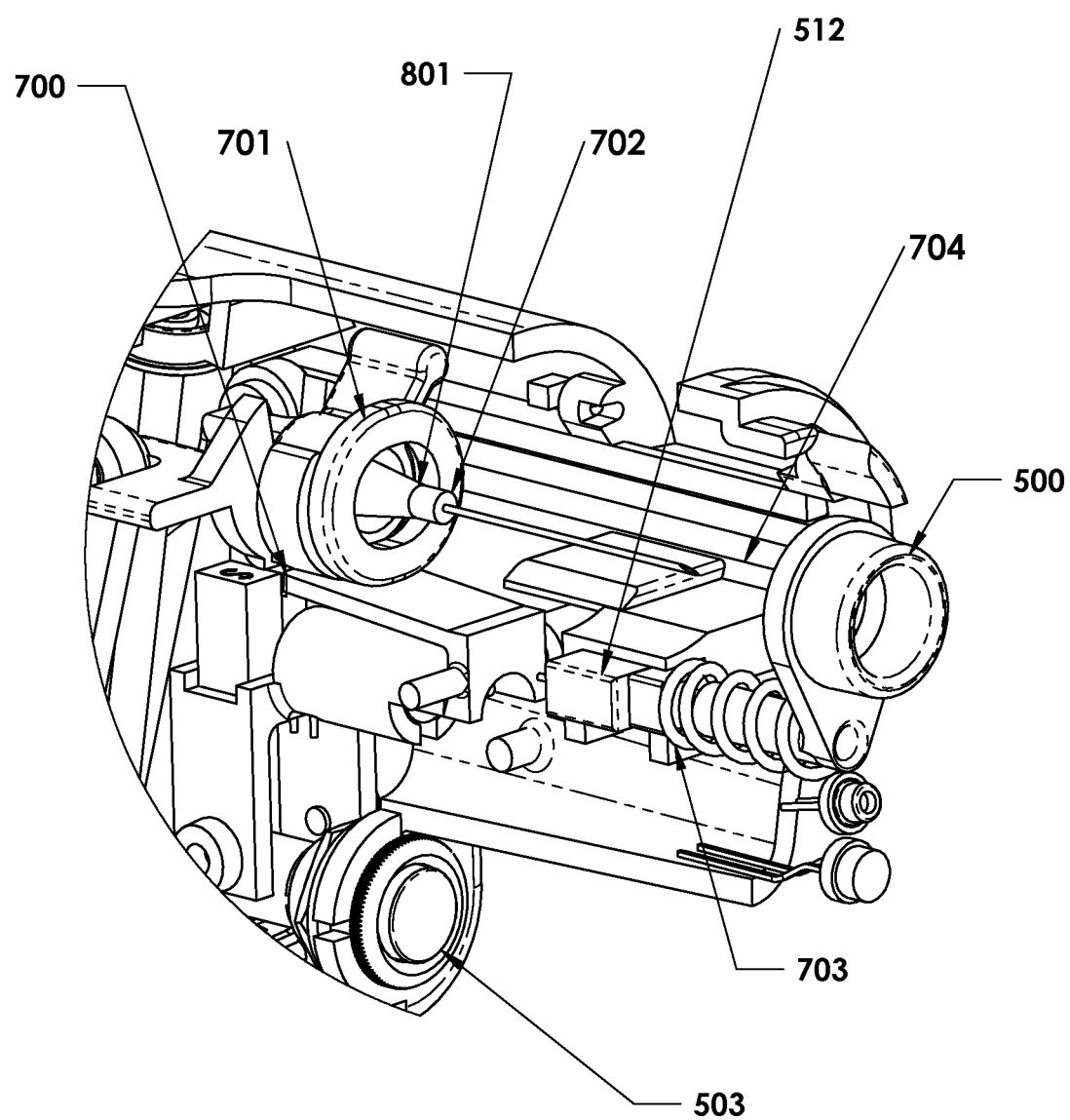
FIG. 8a is a front side alternate perspective view of the preferred embodiment illustrating the interior positioning and actuation components of the handheld applicator device.
Figure 8B:
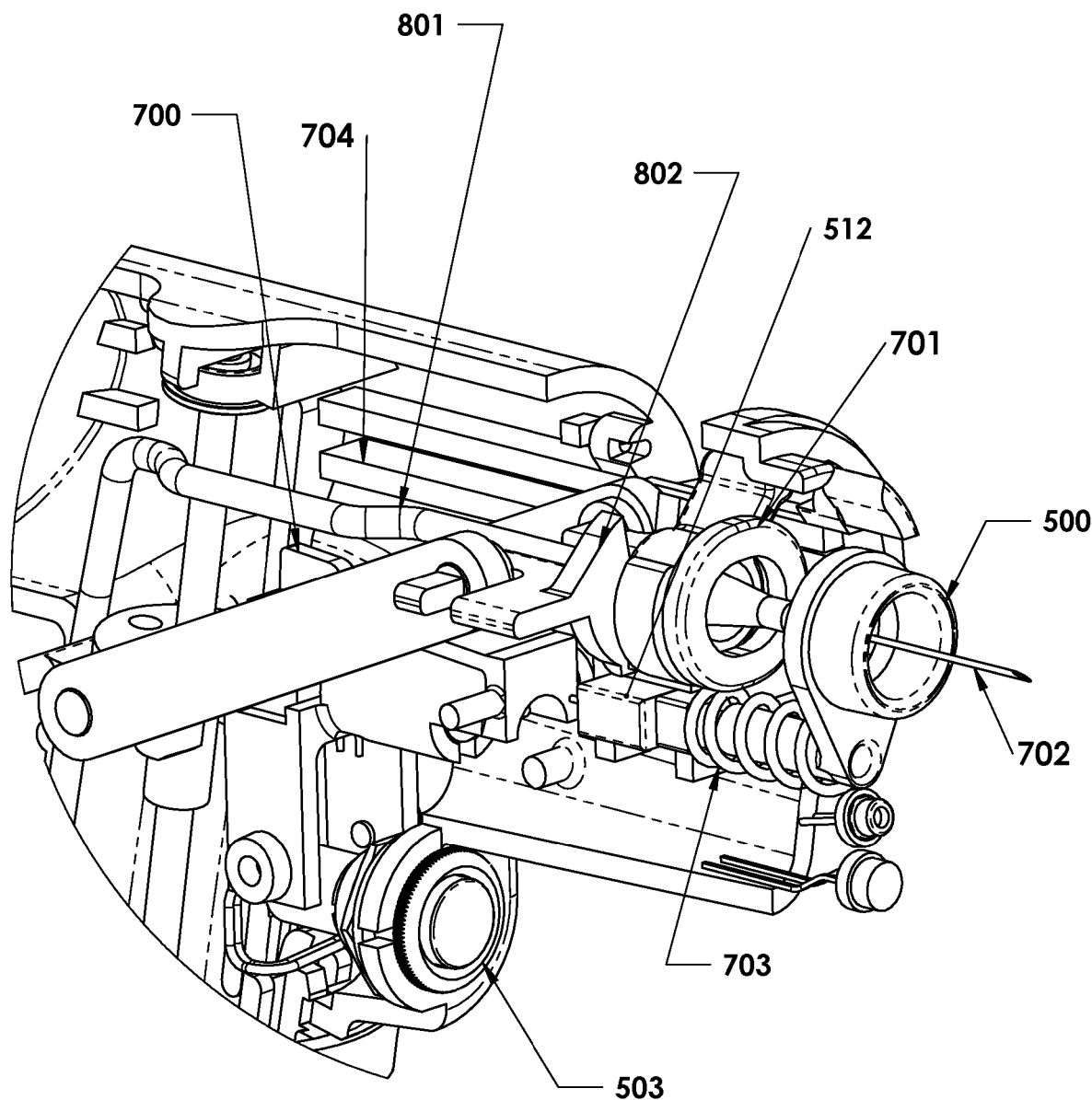
FIG. 8b is a front side alternate perspective view of the preferred embodiment illustrating the interior positioning, disposable tubing and actuation components of the handheld applicator device.

There will be a disposable 801, FIG. 8b, that will be in a sterilized pouch and equipped with a typical vial supply needle, the disposable 801, and the insertion needle 702. The disposable would be used daily, and disposed of at the end of each working day. Thru the use of the bubble sensor 406, FIG. 4a, the disposable 801 will be sensed (no tube, dry tube, wet tube, bubble present, tube primed). Because of desired pumping accuracy, the disposable 801 FIG. is a onetime use component, defined as a single 12 to 16-hour span on a single calendar day.

Figure 4A:
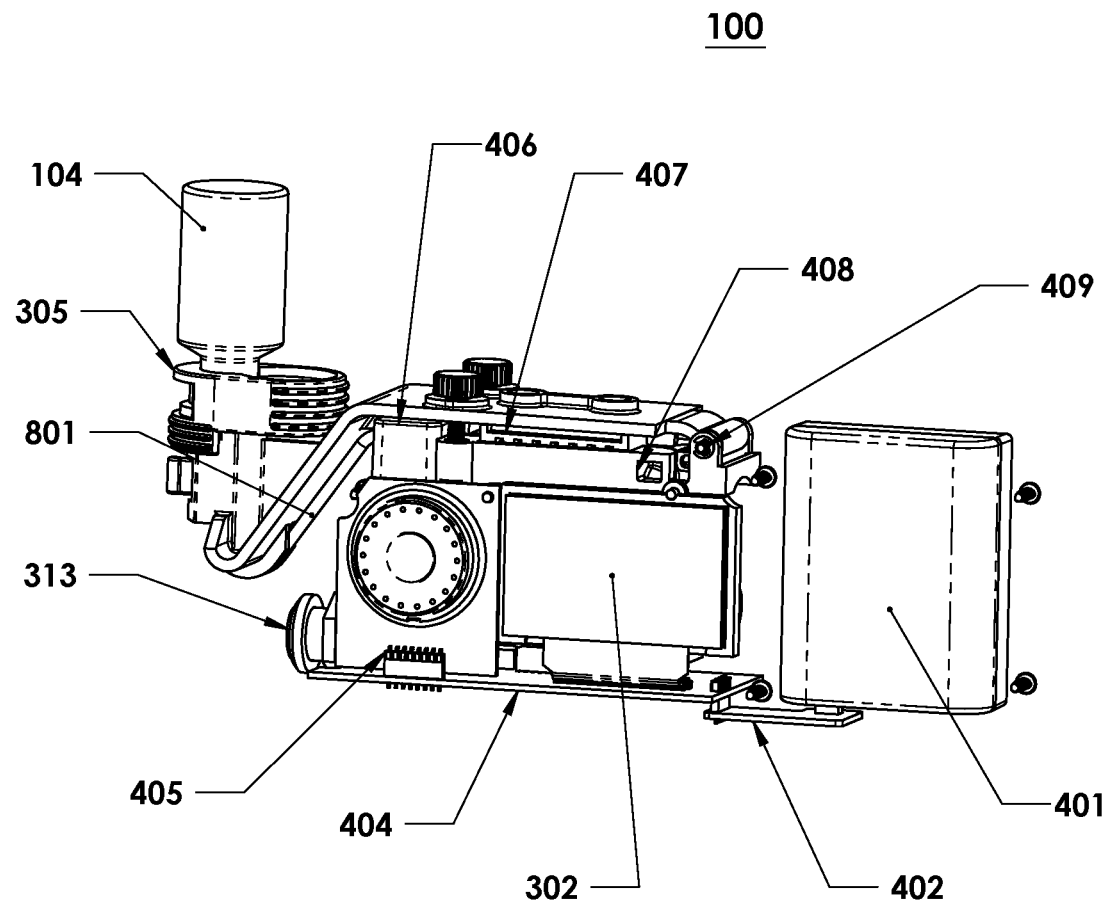
FIG. 4a is a front side perspective view of the preferred embodiment illustrating the interior components of the pump control module.

The preferred embodiment pump/processor module is further illustrated in FIG. 4a which illustrates the interior components of the pump/processor module 100.

Figure 4B:
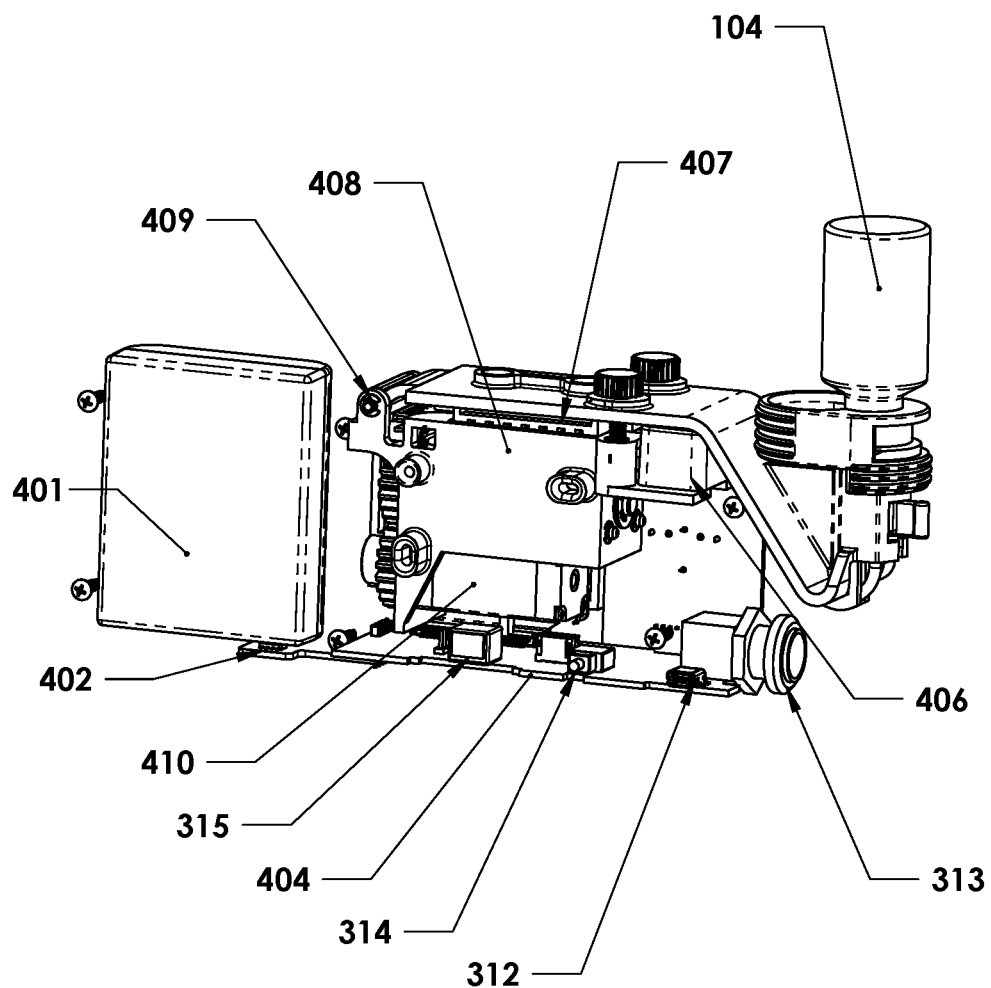
FIG. 4b is a rear side perspective view of the preferred embodiment illustrating the interior components of the pump control module.

In this front view shown in FIG. 4a, the interior components included are the battery 401, battery connector PCB 402, display 302, main PCB 404, selector switch PCB 405, hand-piece connector cable 313, bubble sensor 406, platen 407, pump 408 and platen frame pivot 409. FIG. 4b illustrates the stepper motor 410.

There will be a display 302 of varying size, either monochrome, zoned color or color. The initial display is expected to be the Hantronix™ 12864-5 OLED.

To start with, there would be an on/off power switch 314 (alternatively, the pick button 303) for power control. LEDs 204, which can be a two or three color LED (like red, yellow, and green), will indicate the system status, at a glance. The same status should be displayed on both the pump/processor module 100, and the hand-piece 103. If the hand-piece 103 is not attached to the pump/processor module 100, the display 302 will display a status message that all components are not assembled for system checks to be completed.

When the pump/processor module 100 is initialized, the display 302 can provide information status for several items at the same time. The initial power up of the day would check battery 401 condition first, the check to see if a disposable 801 is in place, if so, is the disposable 801 wet or dry. If the disposable 801 is wet the display will require a new disposable 801 be inserted for the day's use. Once the disposable is current, the display could display several items, such as battery level, injection volume, "priming" vs "on/ready". The pump/processor module 100 will display directions to complete each required step in the use of the IFAS.

The on/off power switch 314 arrangement can have two switch options. There can be a "hard" on/off power switch 314 position (for long term storage or use when moved in a harsh environment), and also have the "momentary" pick button 303 for typical unit control. If the "hard" switch position is in the "OFF" position, there is no power to the main PCB 404. If the on/off power switch 314 is in the "ON" position, the "pick" button 303 would be used to "turn on" the display 302 and pump/processor module 100. The display 302 will display startup information (battery level, self-test, disposable status, etc.), if a disposable 801 is in place (test with the bubble sensor 406), and ready to prime, or replace, if left from the previous day. If no disposable 801 is present, the pump/processor module 100 will prompt the loading of the disposable 801, priming of the disposable 801, then drive the "on/run" functions.

In FIG. 4b, the rear view of the system controller 100 further illustrates the interior components including the battery 401, battery connector PCB 402, main PCB 404, bubble sensor 406, platen 407, pump 408, platen frame pivot 409, stepper motor 410, USB cable connector 312 and hand-piece connector cable 313.

There will be a rechargeable battery pack 401. A ~12 v custom lithium battery pack, similar in shape to the Sony™ NP BG1, will be used, with a two slot battery charging station, included in the system. The battery pack will be easily changeable, in the pump/processor module 100 of the assembly; and, it will be accessible during normal system use.

When the pump/processor module 100 is powered up, the battery 401 state will be checked, if the battery 401 level is low, the display 302 will indicate that a freshly charged battery 401 be installed, and the pump/processor module 100 will not continue without a "fresh" battery 401. Also during use, if the battery 401 level drops below desired levels, the pump/processor module 100 will not continue, and will display "Low Battery Level, Swap Battery". If the battery 401 is exchanged, the condition of the system, prior to the low battery indication, should be resumed. The pump/processor module 100 will verify that the disposable fluid status matches previous status, prior to low battery 401 indication.

Figure 5:
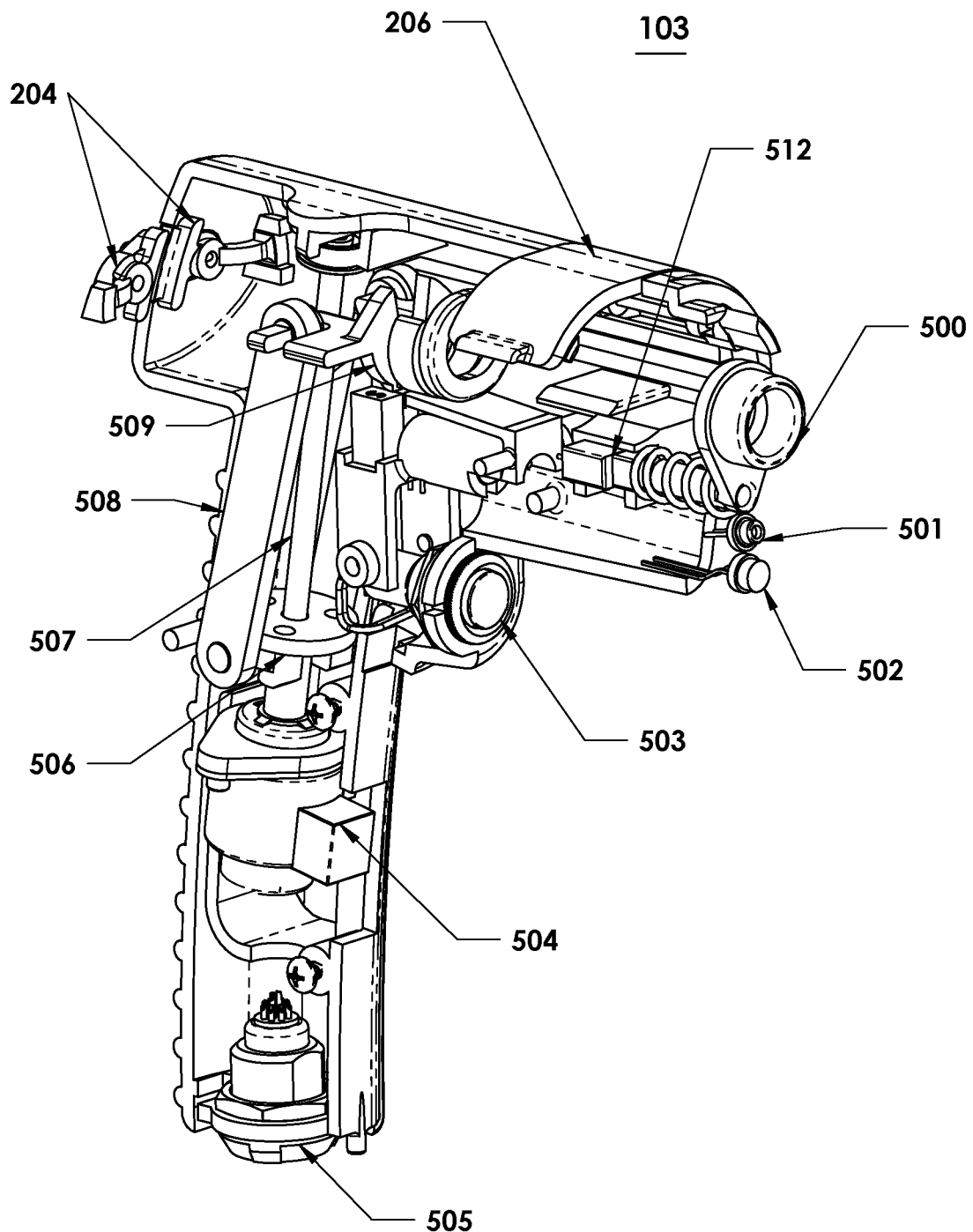
FIG. 5 is a front side perspective view of the preferred embodiment illustrating the interior components of the handheld applicator device.

In FIG. 5, the preferred embodiment is illustrated with an interior view of the hand piece 103. In this view the internal components are illustrated as safety ring 500, laser pointer 501, LED 502, actuation switch 503, hand-piece stepper screw motor 504, hand-piece connector cable connector 505, lead screw nut 506, lead screw 507, actuation arms 508, needle carrier 509, LED indicator lenses 204, needle carrier access door 206 and safety switch 512.

The hand-piece 103 will contain a Haydon™ type hand-piece stepper screw motor 504 to move the insertion needle 702, positioned on a carriage 701 running on a set of ribs 704 to deliver the insertion needle 702 to the target 600, an LED 502 for use as a flashlight, LED indicator lenses 204 which are multicolor to indicate status, optional vibration motor, a "momentary" pick button 303 and pressure activated safety ring 500 to operate as a safe function, and a laser pointer 501 are envisioned.

Once the "on/run" status is reached, the LED 502 and laser pointer 501 can be started automatically or turned on manually. If the unit is built without the "Hard" on/off power switch 314, the pick button 303 would be used exclusively to "turn on" the pump/processor module 100.

The display 302 and corresponding LED indicator lenses 204 will display "system ready", "injection cycle in process", or "error occurred". Solid green LED 204 indicates the pump/processor module 100 is considered ready to use. Solid red LED 204 may be used to indicate the unit is ready to scan for an RFID tag present. The display 302 could also indicate "READY". In addition to the LED indicator lenses 204 and display 302 indications, it would be viable to also implement a vibration motor to let the user "feel" the cycle confirmation (start cycle "two short vibrations", cycle ended "one long vibration", cycle not completed "5-6 short vibrations".

Figure 6:
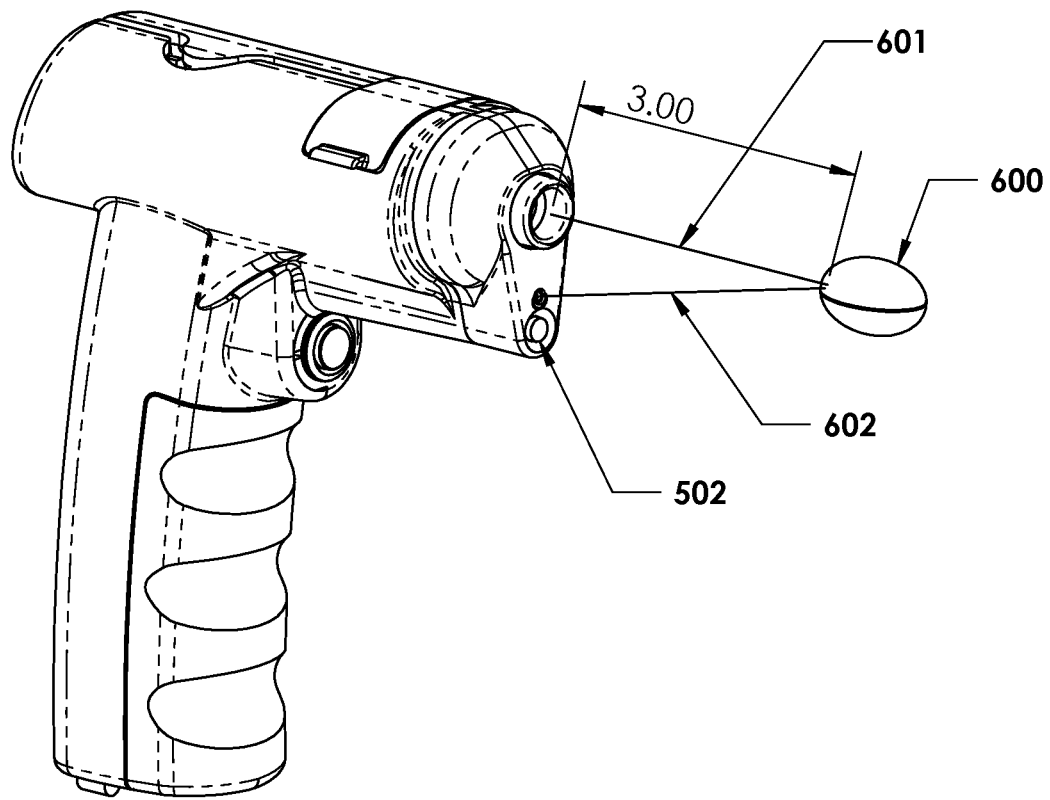
FIG. 6 is a front perspective view of preferred embodiment illustrating the handheld applicator device centerline alignment objective.

In FIG. 6, the preferred embodiment is shown with the hand-piece 103 position towards the injection target 600 with illustration of the alignment of the centerline of needle 601 and corresponding centerline of laser 602.

The display 302 and solid green LED state of the LED indicator lenses 204 which are envisioned as bi/tri-color LEDs, can be used to indicate "injection/ready", "power on", check "Fluid supply", or error states, with a blinking red LED and display verbiage. A third color could be used for the intermediate state for fluid refill, or low battery. The same information offered by the LED status indicators 204, would be shown on the display 302 in word form.

For selection of the dose size, the dosage would be selected with the selection wheel 304 and the display 302 will provide the method to set and indicate injection volume that the user would have access to. The display can indicate different volumes of fluid that will be dispensed. These volumes could be adjustable during calibration, with adjustments applied using the software interface, or by linking the company PC/laptop to the pump/processor module 100.

Both the volume of material to be dispensed and the speed of the stepper screw motor 504 should be adjustable as well, to mimic the clinical examples.

Figure 7:
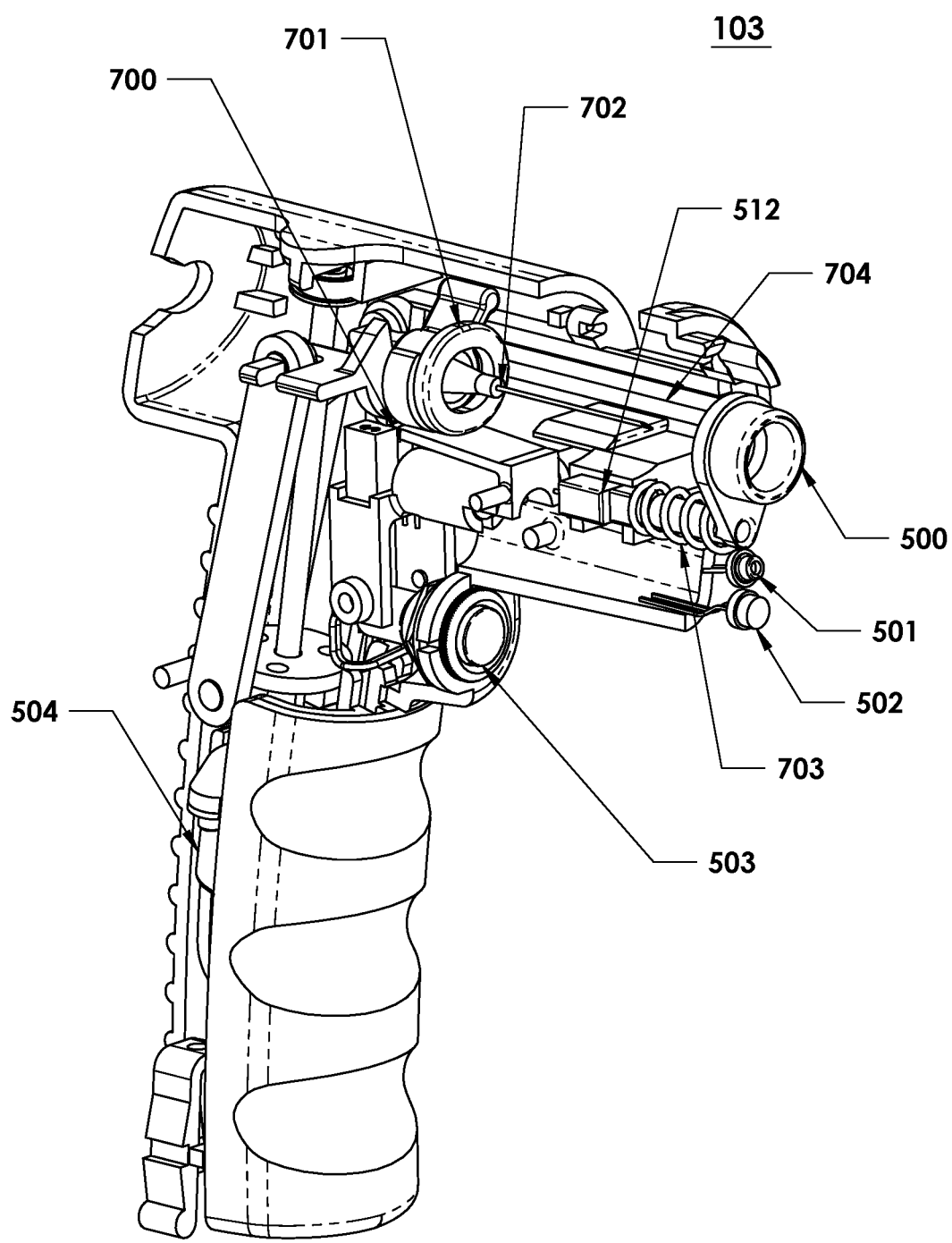
FIG. 7 is a front side perspective view of the preferred embodiment illustrating the interior positioning and actuation components of the handheld applicator device.

FIG. 7 further illustrates the hand-piece 103 internal components including the home position sensor 700, safety switch 512, safety switch spring 703 and actuation switch 503.

In FIG. 8a, a closer view of the hand-piece 103 interior components illustrating the safety ring 500, actuation switch 503, safety switch 512, home position sensor 700 and the carrier 00% position 800, reflecting a fully retracted needle 702.

In FIG. 8b, a similar closer view of the hand-piece 103 interior components illustrating the safety ring 500, actuation switch 503, safety switch 512, home position sensor 700, disposable tubing 801 and carrier 70% position 802, reflecting an extended needle 702.

The hand-piece 103 provides the user interface to dispense the material contained in the vial 104. The hand-piece 103 will have a "contact/pressure" device, the safety ring 500 surrounding the exit point for the insertion needle 702 that must be pressed against the target 600 to operate, and held against the injection site, to activate the injection cycle. If the hand-piece 103 is held in such a way that the trigger 503 function (injection) button were depressed without actuating the "contact/pressure" safety ring 500, the pumping cycle would not begin, and an error tone/vibration and red blinking LED 204 would be initiated.

After the "contact/pressure" safety ring 500 is pressed against the target 600, the trigger 503 function (injection) button is pressed and held to start and complete the injection cycle. The injection cycle advances the insertion needle 702 and initiates the pump 408. The speed of advancement of the insertion needle 702 should be adjustable to mimic a veterinarian inserting the insertion needle 702 manually.

The end of cycle will end with the retraction of the insertion needle 702 (reverse power to the linear stepper motor 504. If the momentary actuation switch 503 were released early, the injection would stop, and the needle would retract to the carrier 00% position 800, and provide the "Error" indicators (LED color, displayed Error note and vibration motor).

Figure 9:
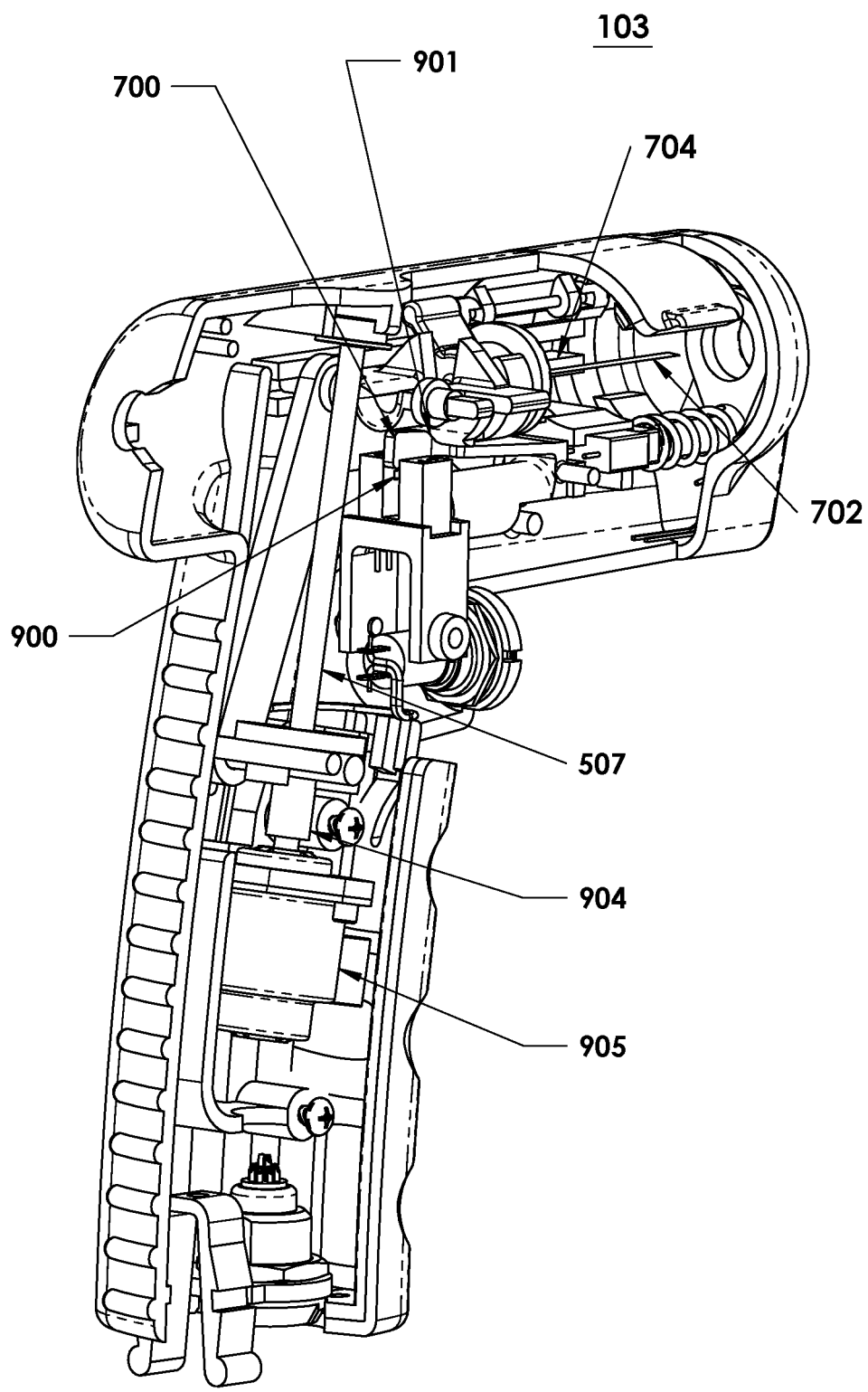
FIG. 9 is a rear side perspective view of the preferred embodiment illustrating the homing function applicable within the handheld applicator device.

FIG. 9 illustrates the present embodiment hand-piece additional components including the home position blade 700, carriage actuation ramp 901, home position sensor 700, hand-piece stepper motor shaft 507, hand-piece stepper motor shaft screw nut 506, and hand-piece stepper motor 504.

It may be advantageous to set forth definitions of certain words and phrases used in this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

What has been described above includes examples of the claimed subject matter. It is, of course, not possible to describe every conceivable combination of components or methodologies for purposes of describing the claimed subject matter, but one of ordinary skill in the art can recognize that many further combinations and permutations of such matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

I claim:

1. A portable apparatus which is used to administer injections to animals comprising:

a trigger controlled hand-piece configured to house an injection needle;

a tube that is configured for connecting said injection needle to a vial that holds an injection liquid, wherein said tube is configured to be removed by a user;

a continuous flow pump that is configured to control a movement of said injection liquid from said vial to said injection needle; and an electronic controller that is configured to advance said injection needle in a first direction for administering an injection to a first animal and retract said injection needle;

wherein said electronic controller is configured to adjust a path of said injection needle in said first direction;

wherein said electronic controller is configured to control said continuous flow pump to administer a first volume of said injection liquid from said vial to a first animal and subsequently administer a second volume of said injection liquid to a second animal from said vial.

2. The portable apparatus of claim 1 wherein said adjustment of said path of said injection needle further comprises adjusting a depth of said injection needle into said first animal.

3. The portable apparatus of claim 1 further comprising a data processor for identifying said first animal and said second animal and storing said first volume of said injection liquid administered to said first animal and said second volume of said injection liquid administered to said second animal.

4. A portable apparatus which is used to administer injections to animals comprising:

a portable housing comprising an injection needle that is configured to be held by a user;

a tube that is configured for connecting said injection needle to a vial that holds an injection fluid, wherein said tube is configured to be removed by the user;

a continuous flow pump that is configured to control a movement of said injection fluid from said vial to said injection needle; and an electronic controller that is configured to control a path of said injection needle in a first direction for administering an injection to a first animal and in a second direction for retracting said injection needle;

wherein said electronic controller is configured to control said continuous flow pump to administer a first volume of injection fluid from said vial to a first animal and subsequently administer a second volume of injection fluid to a second animal from said same vial.

5. The portable apparatus of claim 4 wherein said continuous flow pump is further configured to administer a different said first volume of said injection fluid from said vial than said second volume of said injection fluid from said vial.

6. The portable apparatus of claim 4 wherein said continuous flow pump is further configured to recover said injection fluid from said tube after said administration to said first animal and to said second animal.

7. The portable apparatus of claim 4 wherein said electronic controller is further configured to adjust a path of said injection needle in said first direction for said administration of said injection into said first animal and said second animal.

8. The portable apparatus of claim 7 wherein said adjustment of said path of said injection needle further comprises adjusting a depth of said injection needle into said first animal during said administration.

9. The portable apparatus of claim 7 wherein said adjustment of said path of said injection needle further comprises adjusting a speed of said injection needle into said first animal during said administration.

10. The portable apparatus of claim 7 further comprising a motor that is configured to be connected to said electronic controller and is configured to adjust said path of said injection needle in said first direction.

11. The portable apparatus of claim 7 further comprising a sensor within said portable housing that is configured to sense a location and said path of said injection needle.

12. The portable apparatus of claim 4 further comprising a data processor that is configured for identifying said first animal before said administration of said injection into said first animal.

13. The portable apparatus of claim 4 further comprising a data processor that is configured for identifying said first animal and said second animal and storing said first volume of said injection fluid administered to said first animal and said second volume of said injection fluid administered to said second animal.

14. The portable apparatus of claim 13 wherein said data processor is further configured for recording a first time that said first volume of said injection fluid was administered to said first animal and a second time that said second volume of said injection fluid was administered to said second animal.

15. The portable apparatus of claim 4 further comprising a battery that is configured to provide power to said portable housing, said continuous flow pump, and said electronic controller.

16. The portable apparatus of claim 15 further comprising a pouch that is configured to be worn by said user and is configured to hold said continuous flow pump, said electronic controller, and said battery.

* * * * *